United States Patent [19]
Showalter et al.

[11] 4,045,997
[45] Sept. 6, 1977

[54] AIR CURTAIN DEVICE

[75] Inventors: Lane Crawford Showalter; John Leslie Brokenshire, both of Waterloo; Geoffrey B. Watts, Kitchener, all of Canada

[73] Assignee: Marsland Engineering Limited, Canada

[21] Appl. No.: 665,997

[22] Filed: Mar. 11, 1976

[51] Int. Cl.² .................................................. G01N 33/22
[52] U.S. Cl. ....................................... 73/23; 340/37 R
[58] Field of Search ............... 73/23, 421.5 R, 432 R; 340/237 R, 239, 279

[56] References Cited

U.S. PATENT DOCUMENTS

| 3,430,482 | 3/1969 | Dravnieks et al. | 73/23.1 |
| 3,725,895 | 4/1973 | Haynes | 73/23 |
| 3,942,357 | 3/1976 | Jenkins | 73/23 |

Primary Examiner—Jerry W. Myracle
Assistant Examiner—Stephen A. Kreitman
Attorney, Agent, or Firm—Wheeler, Morsell, House & Fuller

[57] ABSTRACT

This invention relates to a novel air curtain device suitable for use in detecting certain characteristic vapors emitted from objects, particularly individuals, positioned therein. An air curtain having a uniform velocity profile is set up between first and second cabinets. Vapor detector probes are positioned in one cabinet downstream of the air curtain. Detectable vapors carried by an object, such as a person within the air curtain, are stripped off and transported to the vapor detectors. By positioning the vapor detectors remote from the object, a significantly higher number of objects can be screened using known vapor detection techniques within a given period of time.

9 Claims, 2 Drawing Figures

AIR CURTAIN DEVICE

BACKGROUND OF THE INVENTION

This invention relates to a novel air curtain device suitable for use in detecting certain characteristic vapours emitted from objects positioned therein.

Vapours emitted from the more common explosive materials and certain other contraband substances, unless masked or hermetically sealed, can be detected even though concealed, using known vapour trace techniques. When explosives are carried by a person, for example, the individual's clothing and body becomes rapidly contaminated by the explosive's vapour. This is also true with respect to personal effects in luggage when subjected to vapours emitted from a concealed bomb. Accordingly, vapour detectors or "sniffers" are an acknowledged security instrument, particularly in view of the upsurge in terrorist bombings of buildings, aircraft and the like. Their principal use and application is where a large number of personnel or other objects must be quickly screened such as is normally encountered at airport terminals.

One major drawback inherent in vapour detectors used in screening personnel is the fact that each person must be subjected to individual search. Personal search is unacceptable to many and is of major concern to airport supervisors and attendants charged with the responsibility of orderly and rapid air-traveller and luggage processing.

BRIEF SUMMARY OF THE INVENTION

In accordance with this invention, the detection attributes of known vapour detectors is retained, notably their ability to detect certain characteristic trace vapours of selected contraband. The need for hand-held vapour probes is, however, dispensed with; resulting in significantly faster vapour detection processing of people or objects. This is achieved by positioning one or more of the vapour detectors remote from the object being sampled for trace vapours. Through the instrumentality of the air curtain, trace vapours enveloping the object are effectively stripped off and transported in relatively undiluted form to one or more of the remotely positioned vapour detectors. As the stripping off and transport of the vapours to the detectors is finite, the time otherwise taken in manually "sniffing" a large number of individuals or objects is reduced. Further, fewer operators or attendants are required and less operator fatigue is encountered. As the air curtain device of this invention is relatively innocuous in appearance, another advantage of this invention is that individuals do not undergo the same type of personal affront experienced from individual search and indeed, many individuals would not necessarily be aware of the type of search being undertaken unless appropriate inquiries were made.

While the air curtain device of this invention may have many different modes of use, as indicated above, its prime purpose is to screen personnel, such as air travellers. This is achieved by defining a walkway between spaced apart first and second cabinets. One vertical wall of the first cabinet is provided with an air discharge grill while a vertical wall of the second cabinet directly opposed to the first contains a corresponding and complementary air intake grill. Air intake means on the first cabinet upstream of the air discharge grill draws in ambient air and expels it through the outlet grill. This expelled air is then drawn in through the air intake grill of the second cabinet by virtue of air exhaust means located on the second cabinet downstream of the air intake grill. As the air intake and air discharge means are synchronized, a continuous air curtain having a uniform velocity profile is effectively set up between the opposed grills of the two cabinets. Means for detecting specific vapours, such as one or more vapour detector probes, are positioned intermediate the air intake grill and the air exhaust means and carry out their sample and analyze functions in a known manner.

In operation, when an object or individual is positioned in the air curtain for a finite period, vapours enveloping the object are stripped off by the continuous air curtain stream and transported to the vapour detectors. Based on the principle of laminar flow, provided the object is not of a size sufficient to destroy the integrity of the air curtain, stripped vapours are transported to the detector with a minimum amount of dilution. In screening personnel for explosives' detection employing vapour detectors, it has been found that air discharge and air intake grills having a perimeter size of 8 inches $\times$ 5 feet are adequate when operating with an air curtain flow rate of 2 feet per second.

Since a uniform air velocity profile is important, the opposed grills preferably are identical in lattice configuration in order to maintain the integrity of the air curtain. Turbulence within the curtain is further reduced where the depth of each aperture in the lattice-work is approximately four times its cross-sectional dimension. With a view to again further enhancing the uniform flow of air in the air curtain, one or more perforated baffles, such as expanded metal screens may be positioned upstream of the air discharge grill and downstream of the air intake grill intermediate their respective air intake and air discharge means. Where baffles are employed in the second cabinet, it is preferred to position the vapour detector probes between the baffles and the air intake grill so that vapour samples are taken in a relatively quiescent (as opposed to turbulent) air flow. while not essential, it is also preferred to locate the vapour detector probes centrally of the air curtain as it is in this area where the concentration of the vapours to be detected is at its highest. More than one detector probe may be required if it is also desirable to monitor the entire vertical height of the air curtain.

The air intake and air exhaust means should function so as to ensure or further enhance a uniform air velocity profile of the air curtain. This may be achieved, for example, by positioning a plurality of vertically aligned and spaced apart fans in a wall of the first cabinet opposed the air discharge grill and complementary vertically aligned and spaced apart fans in a wall of the second cabinet opposed to the air intake grill.

Transient drafts and external turbulence tending to upset the integrity of the air curtain may be diminished through the use of vertical panel sections (draft wings) associated with each cabinet and the provision of a roof or top section which interconnects the two cabinets. For portability purposes, the two cabinets may also be mounted in fixed relationship on a base so that the entire device can be moved from station to station without re-alignment difficulties.

When the air curtain device of this invention is used in the screening of personnel, in order to obtain proper vapour stripping and hence maximum sensitivity, each individual is obliged to remain stationary in the air curtain for a finite period of time; say two to three seconds.

Accordingly, it is necessary to instruct personnel passing through the device on the steps required of them. This may be carried out by means of an attendant on duty instructing each person, or by the use of barrier gates or other instructional indicia such as stop and go signals associated with the device that indicate to the individual when and where he should stop and when he is entitled to proceed.

The various vapour detector equipment, including the detector controls, electronics, gas supply and alarm means may be conveniently mounted within, on or in cabinet sections associated with the two cabinets. Further, master control equipment and alarm (vapour present) means may be mounted on a console remote from the air curtain device. The remote positioning of at least the alarm from the device is preferred as there is normally a time lag of one to three seconds from the time the stripped and transported vapours enter the probe of the detector and the time the detector has had an opportunity to analyze the vapours so stripped and indicate a positive (vapour present) response or no response. It is preferred that the attendant on duty and the console be located and positioned away from the air curtain device at a point commensurate with the distance one would normally walk after leaving the air curtain and the time at which a response (alarm) or no alarm is registered at the console. If a positive response is registered, the individual can be conveniently intercepted for further screening.

BRIEF DESCRIPTION OF THE DRAWINGS

Exemplary embodiments of the invention will now be described in connection with the accompanying drawings wherein.

DETAILED DESCRIPTION OF THE DRAWINGS

With reference to the drawings, two cabinets, generally designated by arrows 1 and 2 are mounted on a platform 3 in opposed relationship sufficiently spaced apart to allow passage of individual 4 therethrough.

Figure 2:
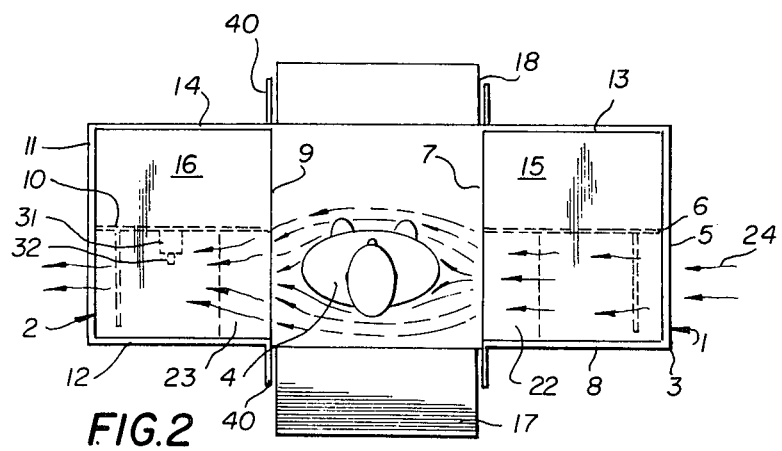
FIG. 2 is a plan view of the air curtain device illustrating the laminar flow effect experienced when an individual is positioned intermediate the opposed cabinets.

The first cabinet, cabinet 1, is defined by four vertical walls 5, 6, 7 and 8, the latter wall also including a front service door. The second cabinet, cabinet 2, is similarly constructed, having four vertical side walls 9, 10, 11 and 12; wall 12 also including a front service door as illustrated. As best seen in FIG. 2, the first and second cabinets may also advantageously include rear cabinet sections which in the case of cabinet 1 is defined by vertical walls 5, 6, 7 and 13; the rear cabinet section of cabinet 2 being formed from vertical walls 9, 10, 11 and 14. Each of rear vertical walls 13 and 14 preferably also include service doors (not shown) the purpose of which will be apparent hereinbelow. The top and bottom of cabinets 1 and 2, and the rear cabinet sections thereof, are closed at their respective tops by top walls 15 and 16 and at their bottoms, by platform 3.

Ingress ramp 17 and egress ramp 18 are pivotally connected to platform 3 between cabinets 1 and 2. In order to move the air curtain device from station to station, ingress and egress ramps 17 and 18 are merely pivoted upwards so that the device may be readily pushed to a new location on casters 19. In the operating mode, ramps 17 and 18 are swung downwardly in order to define a walkway between the two cabinets. Wings 40 extending outwardly from the cabinets tend to protect the integrity of the air curtain from external drafts.

Vertical wall 7 of cabinet 1 is provided with an air discharge grill 22. In a like manner, vertical wall 9 of cabinet 2 also includes a corresponding and complementary air intake grill 23 which is directly opposed and aligned with grill 22. Grills 22 and 23 may be formed from commercially available honeycomb mesh preferably having a hole depth approximately four times the hole diameter in order to present a uniform air velocity profile across the two opposed cabinets 1 and 2 in the direction of arrows 24 as discussed in greater detail below.

We have found that a grill dimension of approximately 5 feet in height and 8 inches in width is dimensionally adequate as an air curtain for the purpose of stripping off vapours from individuals positioned therein. A space of approximately three feet between opposed grills 22 and 23 has also been found satisfactory to permit passage of individuals therethrough without materially upsetting the flow of air from grill 22 to grill 23.

Air intake means is provided on the first cabinet 1 upstream of grill 22 and in the embodiment illustrated, comprises a number of vertically aligned intake screens 25 covering rectangular holes 26 in wall 5. Included with the air intake means, but not illustrated for the sake of clarity, are air intake fans, (not shown) corresponding in number and positioned over rectangular holes 26 internally of cabinet 1. The purpose of the fans is, of course, to draw ambient air internally of cabinet 1 for discharge through grill 22. A similar arrangement exists in cabinet 2 whereby vertically aligned discharge screens 27 cover rectangular holes 28 in wall 11. Air exahust fans (not shown) are positioned over rectangular holes 28 internally of wall 11, in order to discharge the incoming air curtain air entering cabinet 2.

While the number of rectangular holes 26 and 28 together with their corresponding fans may vary, we consider a minimum of three, and preferably five holes in each cabinet to be suitable in setting up a uniform air curtain flow. The fans in each cabinet are synchronized so that the ambient air intake at the first cabinet substantially equals the amount of air exhausted from the second cabinet.

Due to the action of the intake fans and the fact that they are vertically spaced, ambient air entering the first cabinet through rectangular holes 26 is relatively turbulent. This is also the case with the exhaust fans in the area immediately upstream of rectangular holes 28 in cabinet 2. In order to modulate the air in both cabinets, one or more perforated baffles, such as baffle 29 in cabinet 1 and baffle 30 in cabinet 2 are provided. These baffles are positioned proximate wall 5 donwstream of holes 26 and its associated fan and proximate wall 11 upstream of rectangular holes 28 and their associated fans. Since the perforations in the baffles are relatively small, they set up a relatively uniform air flow velocity profile as it passes from baffle 29 through grills 22 and 23 to baffle 30.

Figure 1:
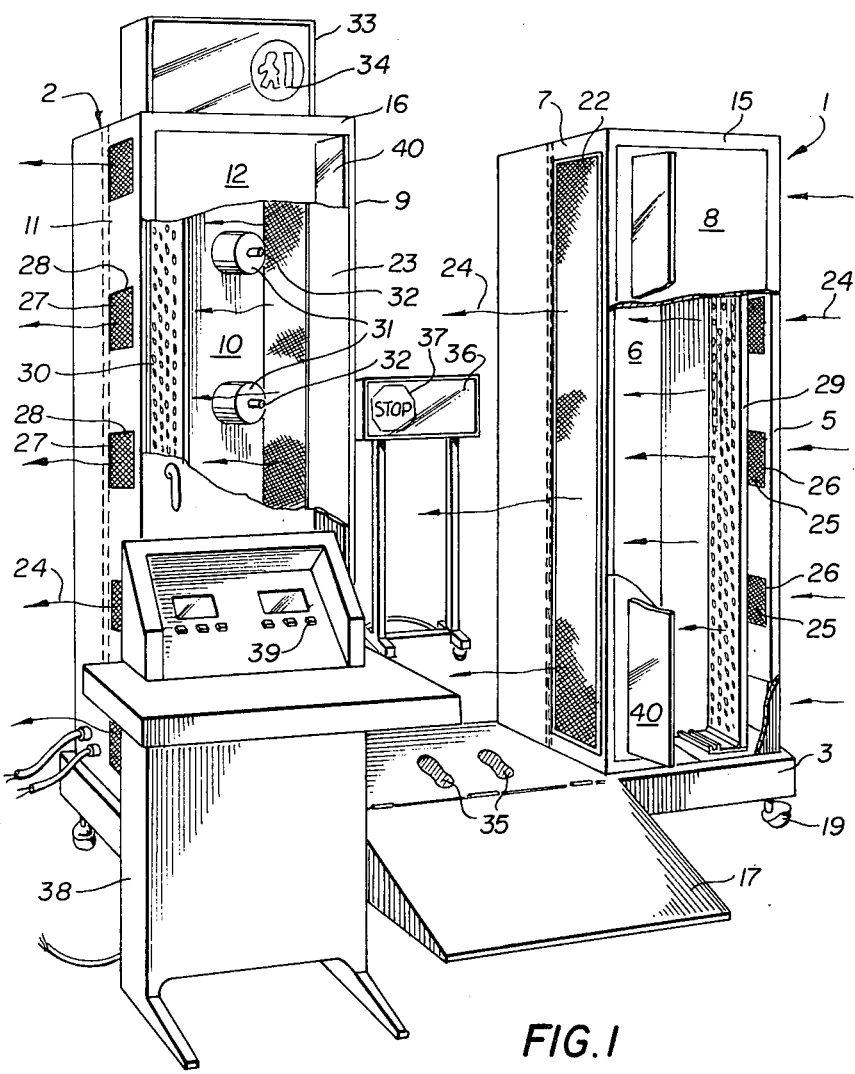
FIG. 1 is a front perspective view, illustrated in partial cut-away, of the air curtain device together with the operator's console and signaling indicia for personnel passing therethrough.

Located intermediate grill 23 and baffle 30 and extending inwardly of the second cabinet from wall 10 thereof are a series of vertically aligned and spaced apart vapour detector probes 31 (two only being shown in the cut-away illustration of FIG. 1 but there in fact being three present in the particular embodiment illustrated).

Each probe 31 includes a probe tip 32 which terminates at the mid-point of the cabinet 2 defined between walls 10 and 12.

From the foregoing, it will be appreciated that when the synchronous air intake and air exhaust fans are turned on, the flow of air between the two baffles 29 and 30 including the air curtain traversing grills 22 and 23 is substantially uniform (a flow rate of two feet per second being considered adequate). With reference to FIG. 2, it will also be observed that the air flow, designated by arrows 24, is deflected about the body of the individual 4 in a laminar flow fashion. The air closest to individual 4 is that air which it taken in centrally of grill 23 and continues its flow in the central area of cabinet 2. Thus detectable vapours enveloping the body of individual 4 are effectively stripped off and transported with a minimum amount of dilution to the probe tips 32 which, as previously indicated, are advantageously located centrally of the air-stream so as to render increased vapour detector sensitivity.

While the rearmost wall of cabinet 1 is effectively defined by vertical wall 6 which is also the case concerning vertical wall 10 of cabinet 2, the rearmost or auxiliary cabinet sections as previously described can be used to house the various gas, electrical and mechanical support components (not shown) necessary to operate the vapour detection probes and co-ordinate the signaling equipment both for personnel passing through the device and control of console 38.

In the embodiment illustrated, signalling equipment for the orderly processing of personnel is provided. Ingress indicator 33 mounted on top of cabinet 2 alternately displays stop and enter signals, enter signal 34 only being shown and which informs a person when to enter the device. Not visually apparent prior to standing on foot markers 35 located on platform 3 between opposed grills 22 and 23, is egress indicator 36 positioned behind the device which also alternately displays stop and exit signals, stop signal 37 only being shown. A pressure sensitive switch (not shown) below foot markers 35 causes enter signal to switch off and to be replaced by a stop signal thereby informing the next following person not to enter the device. Through time delay means (not shown) stop signal 37 on indicator 36 remains displayed informing the individual that he should remain stationary on foot markers 35. This delay, which is normally two to three seconds, is required in order to permit the air curtain to strip the vapours enveloping the person on foot markers 35 and to deliver same to the detectors 31 which are now in the sample and analyze condition. After the appropriate delay a momentary audible tone is sounded and at the same time stop signal 37 is switched off and replaced by an exit signal, indicating that the individual may leave. Approximately three seconds after the individual has egressed an audible tone of a different frequency sounds and the stop signal (not shown) of indicator 33 is replaced by enter signal 34 so that the above process can be repeated.

Operator's console 38 including alarm signal 39 normally is located behind the device so that if a positive response by the detectors is recorded, the person leaving the device can be intercepted for further screening.

The orderly monitoring of personnel passing through the devices can also be manually controlled from the console of the automatic processing can be interrupted should the occasion arise. However, it will also be appreciated that other signal control means for processing personnel may be used without departing from the spirit of this invention.

What we claim as our invention is:

1. An air curtain device for use in detecting selected vapours emitted from objects positioned therein, said device comprising first and second spaced apart cabinets, a vertical wall of said first cabinet provided with an air discharge grill, a vertical wall of said second cabinet provided with a corresponding and complementary air intake grill, said air discharge grill being directly opposite to said air intake grill, air intake means on said first cabinet upstream of said air discharge grill, air exhaust means in said second cabinet downstream of said air intake grill, said air intake and air discharge means being synchronized to provide a substantially uniform horizontal flow of air from the first cabinet to the second cabinet, and vapour detection means located intermediate said air intake grill and said air exhaust means.

2. The device as claimed in claim 1 wherein said air discharge grill and said air intake grill comprise identical lattice-work and wherein the depth of each aperture therein is approximately four times its cross-sectional dimension.

3. The device as claimed in claim 1, wherein said air intake means comprises a plurality of vertically aligned and spaced apart fans in a wall of the first cabinet opposed to said air discharge grill and said air exhaust means comprises a corresponding number of vertically aligned and spaced apart fans in a wall of the second cabinet opposed to said air intake grill.

4. The device as claimed in claim 3, further including at least one perforated baffle section intermediate said air discharge grill and said air intake means, and at least one performated baffle section intermediate said vapour detection means and said air exhaust means.

5. The device as claimed in claim 1 wherein said cabinets are vertically elongate and are mounted in fixed spaced relationship on a platform, said first and second elongate cabinets each provided with associated draft wings, a roof section interconnecting the tops of said first and second cabinets, and wherein said platform, wings, cabinets and top section define an individual passageway therethrough.

6. The device claimed in claim 1 including signaling means for instructing individuals when to enter the device, stand stationary intermediate the cabinets, and when to egress from the device.

7. The device as claimed in claim 1 further including operator control means remote from said device for indicating the presence of a specific vapour emitted from an object positioned in the air curtain.

8. The device as claimed in claim 1 wherein said vapour detection means includes at least three vertically aligned and spaced apart vapour detectors, the probe tips of each of which terminate centrally of the air flowing through the second cabinet.

9. The device as claimed in claim 1, wherein each of said first and second cabinets include separate auxiliary cabinet sections.